United States Patent [19] [11] 4,006,748
Schulman [45] Feb. 8, 1977

[54] IMPLANTABLE UNIPOLAR PACEMAKER WITH IMPROVED OUTER ELECTRODE PLATE

[75] Inventor: Joseph H. Schulman, Los Angeles, Calif.

[73] Assignee: Pacestter Systems, Inc., Sylmar, Calif.

[22] Filed: Jan. 29, 1976

[21] Appl. No.: 653,463

[52] U.S. Cl. .................. 128/419 P; 128/405
[51] Int. Cl.² .................................. A61N 1/04
[58] Field of Search .......... 128/404, 405, 416, 417, 128/418, 419 P, 419 PG, 419 PS, 419 R, 419 O, 421, 422, 423

[56] References Cited
UNITED STATES PATENTS

| 3,606,881 | 9/1971 | Woodson | 128/419 P |
| 3,735,766 | 5/1973 | Bowers et al. | 128/419 P |
| 3,788,329 | 1/1974 | Friedman | 128/419 P |
| 3,911,928 | 10/1975 | Lagergren | 128/419 P |
| 3,935,864 | 2/1976 | Lagergren | 128/419 P |

Primary Examiner—William E. Kamm
Attorney, Agent, or Firm—Lindenberg, Freilich, Wasserman, Rosen & Fernandez

[57] ABSTRACT

A unipolar living tissue stimulator of the implantable type with an outer plate electrode which in one embodiment consists of a flat metal plate slotted by slots to form a plurality of electrically conductive strips. Each strip is electrically in contact with any other strip through only a single path. The strips are dimensioned so that any substantially square or circular surface area on any strip is significantly smaller than the total conductive surface area of the plate. Consequently, the heating of the slotted plate due to an external alternating magnetic field is reduced significantly.

19 Claims, 10 Drawing Figures

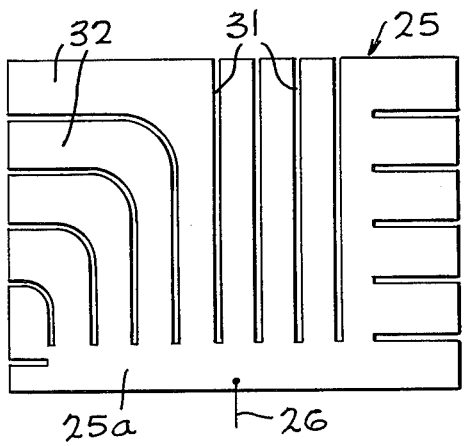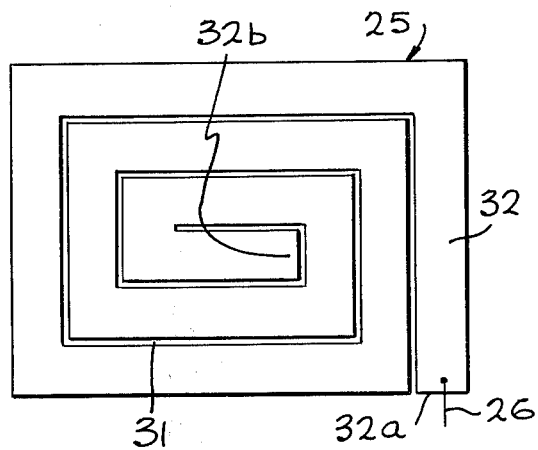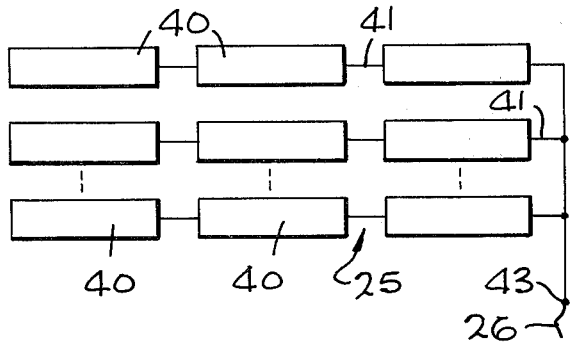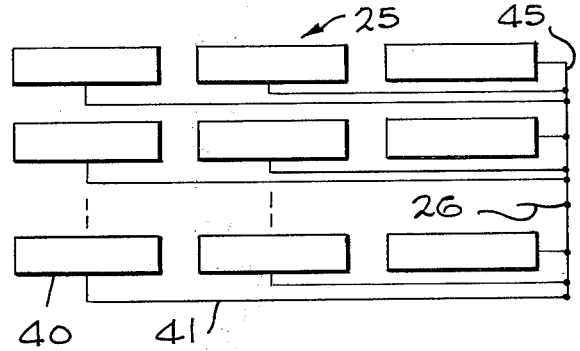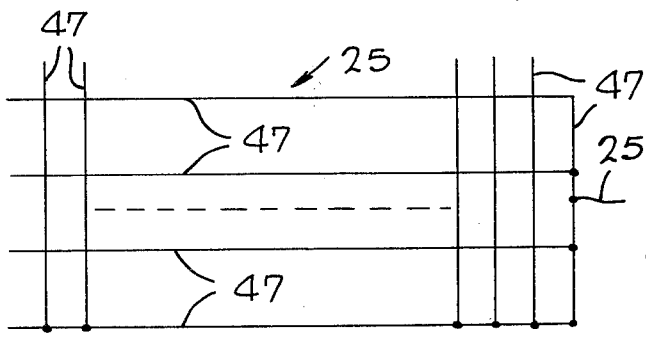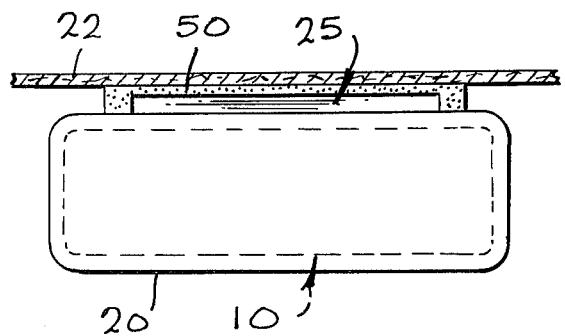

IMPLANTABLE UNIPOLAR PACEMAKER WITH IMPROVED OUTER ELECTRODE PLATE

BACKGROUND OF THE INVENTION

1. Field of the Invention

The present invention generally relates to body stimulators and, more particularly, to an improved body tissue stimulator of the unipolar type which is rechargeable by a magnetic field.

2. Description of the Prior Art

Although the invention relates to various types of body tissue stimulators which are implantable in the body, it will be described in connection with a cardiac stimulator, generally referred to as a pacemaker, for explanatory purposes only, rather than to limit the invention thereto.

As is appreciated, a pacemaker is a device which applies stimulating pulses to the heart. In recent years great advances were made in the development of such pacemakers. At present a pacemaker is available which is implantable in the body and which includes a source of energy, such as a battery, which is rechargeable by an external alternating magnetic field, so that the pacemaker does not have to be removed periodically from the body for battery replacement, thus eliminating the need for frequent surgical operations. One available pacemaker is sealed in a hermetic container so as to extend the life of the pacemaker. During recharging the external magnetic field passes through the hermetic container and is picked up by a pickup coil, which forms part of the recharging circuitry inside the hermetic container.

The aforedescribed hermetically-sealed rechargeable pacemaker is of two types. These include the bipolar type and the unipolar type. As is known in the bipolar type, two electrodes extend from the pacemaker to the heart and each pulse is applied between them. In the unipolar type only one electrode extends to the heart. The other electrode is in the form of an outer electrically conductive metal plate on the side of the pacemaker. The body saline solution and body tissue, which are electrically conductive, provide the return electric path between the electrode in or on the heart and the outer plate, which is electrically connected to the circuitry inside the hermetic container. The outer plate is usually in direct contact with the skin or other body tissue inside the body. One example of a prior art unipolar pacemaker is described in U.S. Pat. No. 3,735,766. In the prior art the outer electrode is formed of a continuous sheet of a biocompatible metal of a sufficiently large area, e.g., several square inches in order to minimize the current density thereat.

In the rechargeable unipolar pacemaker the recharging alternating magnetic field is provided from an external recharging head, which is placed against the body near the location of the implanted pacemaker. Quite often the head is located with respect to the pacemaker so that adequate recharging takes place while part of the magnetic field passes through the outer plate.

OBJECTS AND SUMMARY OF THE INVENTION

It is a primary object of the present invention to provide a new implantable unipolar pacemaker in which the effects of an external alternating magnetic field on the pacemaker outer plate are minimized.

Another object of the present invention is to provide a novel implantable unipolar pacemaker of the type rechargeable by an external alternating magnetic field in which the heating of the outer electrode is minimized.

These and other objects of the invention are achieved by providng a pacemaker of the unipolar type with an outer electrode plate designed so that any substantially square area of the surface of the plate is a very small fraction of the total conductive surface area of the plate. In one embodiment this is achieved by slotting the outer electrode metal plate with narrow slots so that the plate effectively defines elongated rectangular narrow strips. Each of the strips is electrically connected to any other strip through only a single conductive path, with all strips being electrically connected to a common junction.

The novel features of the invention are set forth with particularity in the appended claims. The invention will best be understood from the following description when read in conjunction with the accompanying drawings.

BRIEF DESCRIPTION OF THE DRAWINGS

FIGS. 3–9 are top views of different embodiments of the novel outer electrode plate in accordance with the present invention; and FIG. 10 is a side view of another embodiment of a unipolar pacemaker in accordance with the present invention.

DESCRIPTION OF THE PREFERRED EMBODIMENTS

Figure 1:
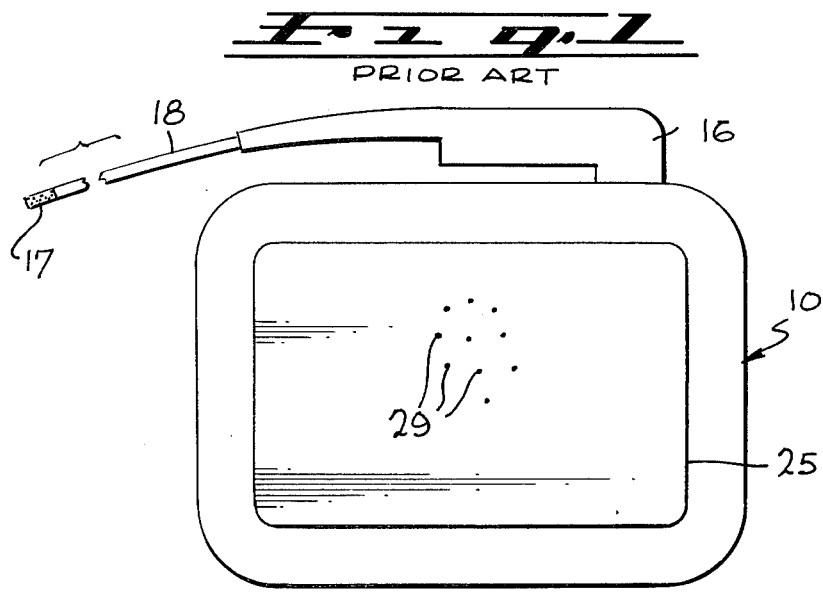
FIGS. 1 and 2 are diagrams useful in explaining a prior art implantable unipolar pacemaker with a conventional outer electrode plate.
Figure 2:
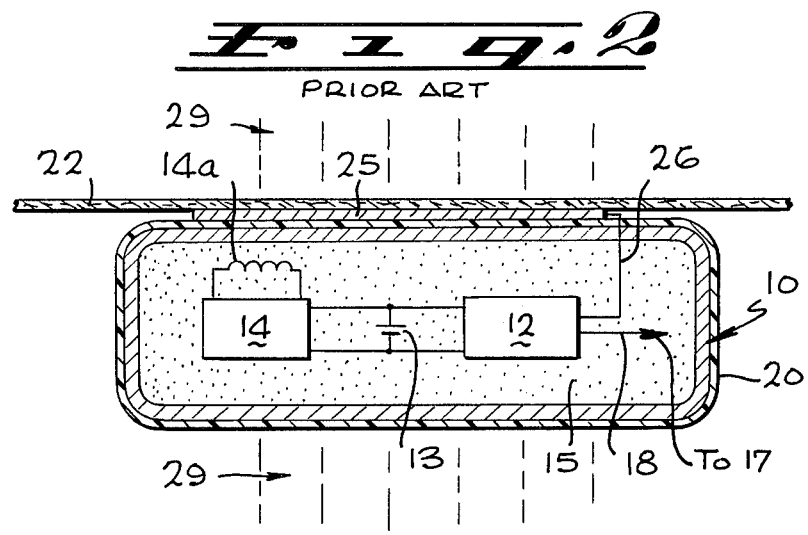

The novel features of the invention and the significant advantages derived therefrom may best be appreciated by first describing a specific embodiment of a prior art implantable unipolar pacemaker. The front view of the prior art pacemaker is shown in FIG. 1, and a cross-sectional view is shown in FIG. 2. The pacemaker, is assumed to be of the rechargeable type by means of an external alternating magnetic field, and hermetically sealed by a hermetic container 10. The latter contains conventional pulse generating circuitry 12, a power source, e.g., a battery 13 and recharging circuitry 14 which are encapsulated by encapsulating matter, e.g., epoxy 15. The recharging circuitry 14 includes a pickup coil, designated by 14a, which picks up the external alternating magnetic field, thereby enabling circuitry 14 to recharge battery 13. The container 10 effectively hermetically seals the contents of the pacemaker from the body saline solution.

Extending from a connector 16, which is attached to the pacemaker container 10 is a single electrode 17 which is connected to the pulse generating circuitry 12 through the connector 16. The electrode lead 18 is sufficiently long so that the electrode can extend to the patient's heart which is to be pulsed. To simplify FIG. 2 the connector 16 is not shown. Only lead 18 is shown connected at one end to circuitry 12. It is obvious that the other end of lead 18 terminates in electrode 17, as shown in FIG. 1. In FIG. 2, the container 10 is shown surrounded by a layer of insulating material 20. Such a layer may be used to provide an optimum bicompatible surface around the container 10 and to provide electrical and/or heat insulation, if that is required.

The unipolar pacemaker, which is generally implanted against the patient's skin 22, includes an outer electrode in the form of an electrically conductive metal plate 25, which is electrically connected to the pulse generating circuitry 12, such as by lead 26. Generally, the lead 26 passes into the container through an appropriate insulated feedthrough. However, with a metal container 10, an alternative to a feed-through is for lead 26 to be connected to the outer surface of the container, which is internally connected to pulse generating circuitry 12.

The body saline solution, which is electrically conductive, provides an electrically conductive return path for the current pulses between the electrode 17 and the outer plate 25 which is exposed to and in contact with the body solution. Since the outer metal comes in contact with the body saline solution and/or body tissue it is formed of a biocompatible metal which provides satisfactory electrical coupling with the saline solution. Some examples of such metals are stainless steel (SS) such as SS 304, cobalt-chromium alloys, titanium, platinum, zirconium and niobium as well as alloys of these metals. Such metals exhibit a resistivity in the microhm-cm range, e.g., from about 60 microhm-cm to about 200 microhm-cm. The typical thickness of a prior art outer electrode plate 25 is on the order of 10 mils or more, with the plate being formed of a continuous sheet of metal of significant surface area, e.g., 2–3 sq. inches. This relatively large surface area is desirable in order to minimize the current density at the plate, so that stimulation, due to the pulses, does not occur at the location of the outer metal plate. In the prior art, the plate is typically circularly shaped or in the shape of a square or wide rectangle.

Experience with the prior art unipolar rechargeable pacemaker has shown that adequate recharging takes place even when the external recharging head, which provides the external magnetic field, is positioned with respect to the implanted pacemaker, so that at least part of the magnetic field passes through the outer plate 25. The alternating magnetic field passing through plate 25 is represented by dots 29 in FIG. 1 and by lines 29 in FIG. 2. Furthermore, it has been found that with the prior art unipolar pacemaker with the plate 25 formed from a continuous sheet of metal when a relatively strong alternating magnetic field is applied for battery recharging purposes, the magnetic field passing through plate 25 generates significant heat in the plate. When the power of the external alternating magnetic field is sufficient to induce power in the pacemaker on the order of about .5 watt or more, e.g., 2–3 watts, the plate heating can be sufficiently great to cause patient discomfort as well as a potential source of damage to body tissue.

The heating of the outer metal plate 25 due to the passage of an alternating magnetic field through it, which is most undesirable, is greatly minimized, if not completely eliminated, by the present invention. In accordance with the present invention an outer metal plate 25 is provided in which the maximum continuous area enclosed by a square or circular boundary on the surface of the plate is restricted to a maximum small value, i.e., is restricted to be very small. The maximum enclosed square or circular area is a very small fraction of the total conductive surface area of the plate 25. Since the largest circular area enclosed within a square area is 3.14/4 of the square area, hereinafter the term "substantially square area" is intended to refer to a square area or to the largest circular area enclosed therein.

Figure 3:
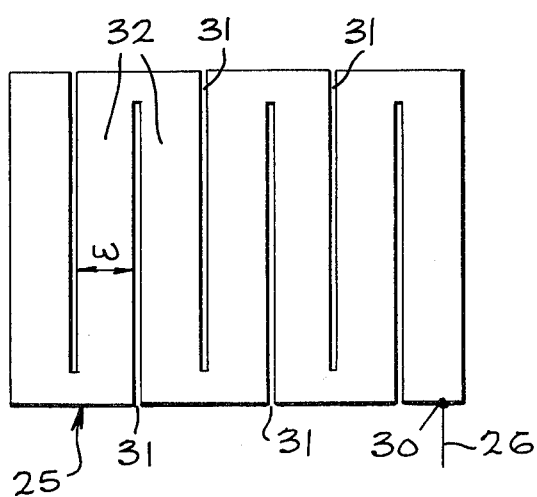

Attention is now directed to FIG. 3 which is a top view of one embodiment of the outer plate 25. For explanatory purposes the plate dimensions are assumed to be 1.5 inch × 2 inches. Thus, the total conductive surface of the plate is 3 sq. inches. The plate 25 is slotted by a plurality of narrow slots 31, shown extending from opposite sides of the plate. These slots effectively convert the plate from a single continuous metal sheet of 3 sq. inches into a plurality of elongated rectangular shaped conductive strips 32. The slots 31 do not extend along the entire plate width in order not to separate the plate into electrically disconnected strips. Rather, each slot 31 extends from one end or side of the plate up to near the opposite plate side. This insures a continuous electrically conductive path for each strip 32 to a common junction 30 to which the lead 26 is connected. The slots 31 in effect convert the plate 25 into the narrow elongated rectangular strips 32. The width W of each strip 32 is quite small as compared with any of the outer dimensions of the total plate 25. Consequently, any substantially square continuous surface area on any of the strips is much smaller than the total surface area of the plate 25.

It has been discovered that by maintaining the maximum substantially square area on the surface of any strip to a small maximum value, the heating of the slotted plate by an external alternating magnetic field is reduced greatly, as compared with the heating of a non-slotted plate of the same metal and thickness when subjected to the same external alternating field. The heating can be reduced to any acceptable maximum level by merely reducing the maximum substantially square area on the surface of any of the strips. This can easily be achieved by merely increasing the number of slots 31. The slots 31 can be made very narrow, e.g., 0.001 inch wide. Thus, their effect on the total conductive surface area of the plate 25 is negligible.

The significant reduction of plate heating in the slotted plate may be highlighted by the following example in which the non-slotted plate is again assumed to be 2 inches by 1.5 inch with a total surface area of 3 sq. inches. By slotting the plate with equally spaced slots extending from the 2 inch sides, 16 separate strips are formed. Neglecting the slots' widths, the width of each strip is about $2/16 = 0.125$ inch. Thus, the maximum square area on any strip surface is only $(0.125)^2 = 0.0156$ sq. inch. On the other hand, the maximum square area of the non-slotted plate is $(1.5)^2 = 2.25$ sq. inches. Thus, with the slots the maximum square area is reduced by a factor of 144. When compared with the total conductive surface area of plate 25 which is 3 sq. inches, the maximum square area (of 0.0156 sq. inches) represents a reduction by a factor of 190.

It should be apparent that by simply increasing the number of slots the maximum substantially square area on the surface of any strip 32 may be made extremely small thereby minimizing the heating of the plate. In the embodiment shown in FIG. 3 by simply doubling the number of equally spaced slots 31, W is reduced by a factor of two so that the substantially square area is reduced by a factor of four. In any practical case the actual maximum substantially square area on any strip surface depends on the heat which is permitted to be generated. Under some conditions a heat reduction by a factor of two from the heat generated in a non-slotted plate may be sufficient. However, it is believed that in most practical applications the plate 25 will be formed so that the substantially square area on any strip will not be more than $1/n$ of the total conductive surface area of the plate, where $n$ will be on the order of not less than 5 and in some cases may be as high as 100 or more.

Figure 4:
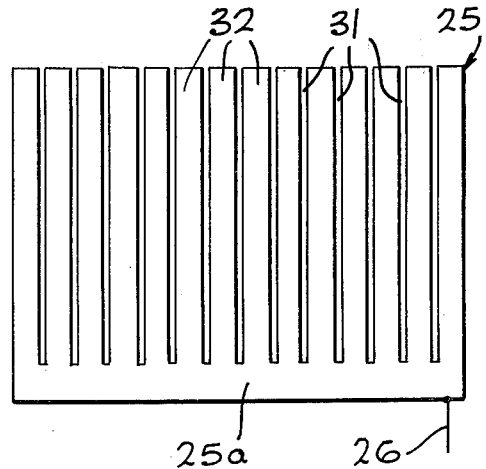

In the embodiment shown in FIG. 3 except for one conductive strip 32 to which the lead 26 is directly connected at junction 30 each other strip 32 is electrically connected to lead 26 through another strip 32. FIG. 4 is a top view of another embodiment of plate 25. It differs from that shown in FIG. 3 only in that the slots 31 all extend inwardly from one side of plate 25. In the embodiment of FIG. 4 each strip 32 is effectively electrically connected to lead 26 through the lower part 25a of the plate 25 rather than through another strip 32. An embodiment similar to that shown in FIG. 4 is shown in FIG. 5. In the embodiment shown in FIG. 5 the slots extend inwardly from three sides of the plate 25.

It should be pointed out that the slotted plate 25 need not serve or function as an electrostatic shield. Rather, it serves as an electrically conductive outer plate for a unipolar pacemaker. When in use it is located in and is in contact with the body saline solution and conducts currents to and from the body saline solution and/or body tissue. In order for each conductive strip 32 to contribute to and form part of the electrically conductive plate 25 it has to have an electrically conductive path to the lead 26 which connects the plate 25 to the pulse generating circuitry 12. It should be stressed however, that each strip 32 should be connected to the lead 26 through a single electrically conductive path without a return current path between any two strips. It is recognized that when in use body saline solution which is electrically conductive is present in the slots 31. However, the resistivity of the metal plate is in the microhm-cm range e.g., 80–200 microhm-cm, while the resistivity of the saline solution is generally on the order of about 20 ohm-cm. Consequently, due to the extremely high resistance of the saline solution as compared with that of the metal plate 25 the body saline solution in the slots 31 does not act as a meaningful current conductor between adjacent strips 32.

Another embodiment of the slotted plate 25 is shown in FIG. 6. Therein, a single continuous slot 31 in the shape of a spiral is formed in the plate 25. It effectively converts the plate into a single long continuous spiral shaped strip 32 whose opposite ends are designated by 32a and 32b of a width W. It should be apparent that the maximum substantially square area on the surface of the strip 32 is not greater than $W^2$, which is only a small fraction of the total surface area of the plate 25. It should further be apparent that if desired instead of using a slotted plate 25 the outer electrode plate may be formed as an elongated narrow electrically conductive strip or wire which may be wrapped around the pacemaker as a coil. The strip should be narrow as compared with its total electrically conductive surface area, so that the largest substantially square area on the strip surface is significantly smaller than its total conductive surface area.

In each of the above described embodiments the separate one or more conductive strips 32 are formed by cutting one or more slots 31 in the plate 25. If desired, the plate 25 may be formed of separate metallic plate members 40 which are interconnected at junction 43 to lead 26 by electrically conductive wires 41, as shown in FIG. 7. If desired, instead of connecting some of the plate members 40 to lead 26 through other plate members, each plate member 40 may be connected through a separate conductive wire 41 to a common wire 45 to which lead 26 is also connected as shown in FIG. 8. In the embodiment shown in FIGS. 7 and 8 the total conductive surface area of the outer plate consists essentially of the surface areas of all the plate members 40. Preferably, each plate member 40 should be shaped as an elongated rectangle, so that any substantially square or circular area on the plate member is small compared to the total area of the plate member.

As shown in FIG. 9 the outer plate 25, providing the advantages hereinbefore discussed, namely reduced heating, may also be formed as a matrix of electrically conductive wires 47. Each wire can be viewed as a long rectangle of minimal width. If one wanted to permit an electrostatic field to pass through the conductive plate with little or no impediment, yet couple the conductive plate to the tissue without generating heat, it can be accomplished here by separating the wires sufficiently to permit electrostatic fields to pass between the wires. Each of these wires may be connected to lead 26 directly or through one of the other wires. However, it should again be stressed that each wire should be electrically connected to any other wire only at one point, so as not to provide a large substantially square or circular loop of continuous wire which would generate heat due to the magnetic field. In the embodiment shown in FIG. 9, the total conductive surface area of the plate 25 consists of the exposed surface areas of all the wires 47.

The novel outer plate of the present invention is also advantageous when forming part of an implantable unipolar pacemaker which is not of the rechargeable type by an external magnetic field. A patient with an implantable unipolar pacemaker may be present where an external magnetic field is present. Such a field may pass through the skin and heat a conventional outer plate. However, when the outer plate of the present invention is used the heating of the plate by such a field would be minimal. Thus, the novel plate effectively protects the patient from discomfort or damage to body tissue even when the patient happens to be present where an external magnetic field exists.

It has been found that when the external alternating magnetic field is relatively strong, such as being large enough to induce 2 watts or more of power in the pacemaker, the maximum substantially square area should not exceed 0.125 square inch in order to minimize plate heating and thereby prevent patient discomfort or potential injury to body tissue. In situations where the external alternating magnetic field is relatively weak, e.g., capable of inducing 0.5 watt or less in the pacemaker, a conventional outer plate, i.e., one formed of a continuous sheet of metal may be used. However, to minimize any patient discomfort or damage to body tissue due to localized heating in the plate, called "hot spots", the conventional outer plate should be coated with an outer layer of plastic type matter which has reasonably low thermal conductivity and is electrically conductive plastic, which comes in contact with the patient skin or other body tissue. A side view of such an arrangement is shown in FIG. 10. The outer plate is designated by 25 and the outer layer of the plastic matter is designated by 50 with the skin being designated by 22. The plastic layer 50 serves two functions. Due to its electrical conductivity, it provides a conductive path between the body saline solution and body tissue to the outer plate 25 due to its low thermal conductivity. In addition, it tends to spread any heating of the plate 25, particularly due to hot spots, over its large surface area, to thereby minimize damage to body tissue or patient discomfort, due to the heating of the plate 25.

The conductive plastic 50 should be of the biocompatible type, resistant to corrosion by the body saline solution, and provide good electrical coupling to the body saline solution. In general its minimum electrical resistivity should be greater than that of the metal plate 25 by a factor $x$, where $x$ is on the order of 10 or more. Its maximum electrical resistivity should be on the order of about 40 times the electrical resistivity of the body saline solution, e.g., 400 ohm-cm. Layer 50 may be formed from implantable medical grade plastics, like silicon rubber, epoxy and like materials containing metallic matter. For example, layer 50 may be formed from epoxy containing steel or zirconium. Preferably, the thickness of the plastic layer 50 should be on the order of 25 mils. If the plastic layer 50 is resistant to flaking or cracking, in some applications it can be used as the outer plate of a unipolar pacemaker even without the underlying metal plate 25. Clearly, when the plastic layer 50 serves as the outer electrode means it has to be electrically connected to the pulse generating circuitry, such as by lead 26 as hereinbefore described. In either embodiment including layer 50 the heating of the outer electrode means due to the external magnetic field is reduced significantly.

Although particular embodiments of the invention have been described and illustrated herein, it is recognized that modifications and variations may readily occur to those skilled in the art and consequently, it is intended that the claims be interpreted to cover such modifications and equivalents.

The embodiments of the invention in which an exclusive property or privilege is claimed are defined as follows:

1. In a unipolar implantable living tissue stimulator of the type including pulse generating means, a stimulating electrode electrically connected to said pulse generating means and locatable at the tissue to be stimulated by pulses supplied to said stimulating electrodes by said generating means, and outer electrode means connected to said generating means and in direct electrical contact with body saline solution which extends from said stimulating electrode to said outer electrode means to thereby provide an electrical conductive path therebetween, the improvement comprising:

outer electrode means defining an electrically conductive surface of preselected area which is in direct electrical contact with the body saline solution when said stimulator is implanted in a body, said outer electrode means defining a plurality of electrically conductive elements whereby any substantially square area on the surface of any of said elements does not exceed a preselected maximum value which is significantly smaller than the total area of the conductive surface of said outer electrode means.

2. The improvement as described in claim 1 wherein said outer electrode means is a metal plate, with a plurality of slots defined therein to separate said plate into a plurality of electrically conductive strips, defining said electrically conductive elements, each strip being electrically connected to any other strip only through a single electrically conductive path, the strips having dimensions whereby any substantially square area of the surface of any strip does not exceed said preselected maximum value which is significantly smaller than the total area of the conductive surface of said metal plate.

3. The improvement as described in claim 1 wherein said outer electrode means is a plate of a biocompatible metal with a plurality of slots extending inwardly from at least one side of said metal plate, to thereby separate said plate into a plurality of electrically conductive elongated substantially rectangular shaped strips, defining said electrically conductive elements, each strip being electrically connected to any other strip through a single conductive path without a return path therebetween, the strips having dimensions whereby the largest substantially square area on the conductive surface of any strip is smaller than the total conductive surface area of said plate by a factor $n$, where $n$ is not less than 10.

4. The improvement as described in claim 3 wherein $n$ is not less than 100.

5. The improvement as described in claim 1 wherein said outer electrode means comprises a plurality of individual electrically conductive metal plates, each of said plates being electrically connected to any other plate through a single electrically conductive path, with any substantially square area on any of said metal plates being significantly smaller than the total surface area of said metal plates, by a factor not less than 10.

6. The improvement as described in claim 5 wherein the substantially square or circular area on any of said metal plates is smaller than the total area of said metal plates by a factor of not less than 100.

7. The improvement as described in claim 5 wherein each of said metal plates is in the shape of an elongated rectangle.

8. The improvement as described in claim 1 wherein said outer electrode means comprises an array of individual electrically conductive wires, each wire being electrically connected to any other wire through a single electrically conductive path, without a current return path therebetween, with the total conductive surface areas of said wires defining the area of the conductive surface of said outer electrode means.

9. In a unipolar implantable living tissue stimulator of the type including pulse generating means and a stimulating electrode electrically connected to said pulse generating means for stimulating living tissue and outer electrode means connected to said pulse generating means and being in contact with body saline solution, the improvement comprising:

said outer electrode means including a sheet of electrically conductive metal of a preselected surface area, and including a layer of electrically conductive matter surrounding and being in direct electrical contact with said sheet of metal and being in direct electrical contact with body saline solution, when said stimulator is implanted in a body, said electrically conductive matter exhibiting heat insulating properties and being characterized by a resistivity which is greater than the resistivity of said sheet of metal by a factor $n$, where $n$ is on the order of not less than 10, and being further characterized by being resistive to corrosion by body saline solution, said layer of electrically conductive matter providing an electrical current path between said body saline solution and said sheet of metal and distributes heating of said sheet of metal over the entire surface thereof.

10. The improvement as described in claim 9 wherein the resistivity of said sheet of metal is substantially in the range 60 microhm-cm to 200 microhm-cm and $n$ is substantially in the range of 100 to 10,000.

11. In a unipolar implantable living tissue stimulator of the type including pulse generating means powered by a source of power rechargeable by an external magnetic field adapted to induce in said stimulator, power on the order of not less than 0.5 watt, the stimulator further including an electrode connected to said pulse generating means and locatable at tissue to be stimulated and outer electrode means connected to said pulse generating means and in direct contact with body saline solution, when the stimulator is implanted in a body, improved outer electrode means to minimize the heating of said outer electrode means due to any portion of said external magnetic field passing therethrough, said improved outer electrode means defining a conductive surface of a preselected area and formed of a plurality of electrically conductive elements having dimensions so that any substantially square area on the surface of any of said elements is smaller than the total area of the conductive surface of said outer electrode means, by a factor $n$ of not less than 5, each of said conductive elements being interconnected to any other element through a singe current path.

12. The improvement as described in claim 11 wherein said outer electrode means is a plate of a biocompatible metal with a plurality of slots extending inwardly from at least one side of said metal plate, to thereby separate said plate into a plurality of electrically conductive elongated strips, defining said electrically conductive elements, each strip being electrically connected to any other strip through a single conductive path without a return path therebetween, the strips having dimensions whereby the largest substantially square area on the conductive surface of any strip is smaller than the total conductive surface area of said plate by the factor $n$, where $n$ is not less than 10.

13. The improvement as described in claim 12 wherein $n$ is not less than 100.

14. In a unipolar implantable living tissue stimulator of the type including pulse generating means and a stimulating electrode, electrically connected to said pulse generating means for stimulating living tissue and outer electrode means connected to said pulse generating means, and being in contact with body saline solutions, when the stimulator is implanted in a body, said outer electrode means comprising a layer of biocompatible matter which is electrically conductive and electrically coupleable to the body saline solution, said matter being characterized by heat insulating properties and by an electrical resistivity in the range of 20 microhm-cm to 400 ohm-cm.

15. The improvement as described in claim 14 wherein the resistivity of said matter is not less than 10 microhm-cm.

16. The improvement as described in claim 14 wherein the electrical resistivity of said matter is not less than 20 ohm-cm.

17. In a unipolar implantable living tissue stimulator of the type including pulse generating means with an outer electrically conductive electrode, which is electrically connected to said pulse generating means and is in electrical contact with body saline solution when the stimulator is implanted in a body, an improved outer electrically conductive electrode comprising electrically conductive matter having a preselected surface area with which the body saline solution comes in contact, said matter being dimensioned whereby any continuous substantially square area on the surface thereof does not exceed a preselected value, said substantially square area being smaller than the total surface area of said electrically conductive matter by a factor not less than ten.

18. The stimulator as described in claim 17 wherein the total surface area of said matter is on the order of not less than 2 square inches and the maximum substantially square area is on the order of not more than 0.02 square inch.

19. The stimulator as described in claim 17 wherein the stimulator is rechargeable by an external alternating magnetic field of sufficient strength to induce a power on the order of not less than 2 watts in said stimulator and the maximum continuous substantially square area is on the order of not more than 0.02 square inch and the total surface area of said matter is on the order of not less than 2 square inches.

* * * * *